US007887534B2

(12) United States Patent
Hamel et al.

(10) Patent No.: US 7,887,534 B2
(45) Date of Patent: Feb. 15, 2011

(54) ELECTROSURGICAL SYSTEM

(75) Inventors: Andrew Hamel, San Mateo, CA (US);
Michael Baycura, San Jose, CA (US);
Chris Earley, Santa Clara, CA (US);
David Hoffman, Santa Cruz, CA (US);
Alexandr Ikriannikov, Castro Valley, CA (US)

(73) Assignee: Stryker Corporation, Kalamazoo, MI (US)

( * ) Notice: Subject to any disclaimer, the term of this patent is extended or adjusted under 35 U.S.C. 154(b) by 1285 days.

(21) Appl. No.: 11/334,755

(22) Filed: Jan. 18, 2006

(65) Prior Publication Data
US 2007/0167941 A1    Jul. 19, 2007

(51) Int. Cl.
*A61B 18/04* (2006.01)
(52) U.S. Cl. .............................. 606/34; 606/32; 606/38
(58) Field of Classification Search ............. 606/32–52; 607/98
See application file for complete search history.

(56) References Cited

U.S. PATENT DOCUMENTS

| | | | | | |
|---|---|---|---|---|---|
| 4,171,700 | A | * | 10/1979 | Farin ........................... | 606/35 |
| 4,244,371 | A | * | 1/1981 | Farin ........................... | 606/35 |
| 4,630,273 | A | * | 12/1986 | Inoue et al. .................... | 372/9 |
| 4,658,815 | A | * | 4/1987 | Farin et al. ................... | 606/34 |
| 4,658,819 | A | * | 4/1987 | Harris et al. .................. | 606/34 |
| 4,727,874 | A | * | 3/1988 | Bowers et al. ................ | 606/38 |
| 4,907,589 | A | * | 3/1990 | Cosman ....................... | 606/34 |
| 5,342,356 | A | * | 8/1994 | Ellman et al. ................. | 606/32 |
| 5,364,392 | A | * | 11/1994 | Warner et al. ................. | 606/34 |
| 5,370,645 | A | * | 12/1994 | Klicek et al. .................. | 606/35 |
| 5,422,567 | A | * | 6/1995 | Matsunaga ................... | 324/142 |
| 5,443,462 | A | * | 8/1995 | Hannant ....................... | 606/34 |
| 5,472,442 | A | * | 12/1995 | Klicek .......................... | 606/42 |
| 5,562,503 | A | * | 10/1996 | Ellman et al. ................ | 439/638 |
| 5,573,533 | A | * | 11/1996 | Strul ............................ | 606/34 |
| 5,584,830 | A | * | 12/1996 | Ladd et al. .................... | 606/34 |
| 5,599,344 | A | * | 2/1997 | Paterson ....................... | 606/34 |
| 5,630,426 | A | * | 5/1997 | Eggers et al. ................ | 600/547 |
| 5,651,780 | A | * | 7/1997 | Jackson et al. ................. | 606/1 |
| 5,713,896 | A | * | 2/1998 | Nardella ....................... | 606/50 |
| 5,749,869 | A | * | 5/1998 | Lindenmeier et al. ......... | 606/34 |
| 5,868,737 | A | * | 2/1999 | Taylor et al. .................. | 606/34 |

(Continued)

FOREIGN PATENT DOCUMENTS

DE          3340891 A1 *   7/1984

(Continued)

*Primary Examiner*—Linda C Dvorak
*Assistant Examiner*—Amanda Scott
(74) *Attorney, Agent, or Firm*—Flynn, Thiel, Boutell & Tanis, P.C.

(57) ABSTRACT

An electrosurgical system comprising, among other things, a control console to which detachably connects one or more electrosurgical probes capable of coagulating and ablating tissue. The control console generates a selectively variable power signal having a duty cycle that is dynamically modulated so as to maintain an average power level of a probe that is lower than a predefined maximum power level. The system can also incorporate both an impedance monitoring system and a current monitoring system as means to detect potentially dangerous situations, as well as a monitoring system for detecting impedance at relatively low power levels upon first activation of the probe. The probe can also incorporate non-volatile memory for storing probe-specific operating parameter data, probe usage data, data restricting probe use, error codes, and control console updates.

20 Claims, 5 Drawing Sheets

U.S. PATENT DOCUMENTS

| | | | | |
|---|---|---|---|---|
| 5,928,159 | A * | 7/1999 | Eggers et al. | 600/547 |
| 5,971,980 | A * | 10/1999 | Sherman | 606/34 |
| 6,040,694 | A * | 3/2000 | Becker | 324/230 |
| 6,123,702 | A * | 9/2000 | Swanson et al. | 606/34 |
| 6,165,173 | A * | 12/2000 | Kamdar et al. | 606/34 |
| 6,183,468 | B1 * | 2/2001 | Swanson et al. | 606/40 |
| 6,383,183 | B1 * | 5/2002 | Sekino et al. | 606/34 |
| 6,413,255 | B1 * | 7/2002 | Stern | 606/41 |
| 6,423,057 | B1 * | 7/2002 | He et al. | 606/34 |
| 6,436,096 | B1 * | 8/2002 | Hareyama | 606/34 |
| 6,488,679 | B1 * | 12/2002 | Swanson et al. | 606/40 |
| 6,494,880 | B1 * | 12/2002 | Swanson et al. | 606/40 |
| 6,508,815 | B1 * | 1/2003 | Strul et al. | 606/34 |
| 6,511,478 | B1 * | 1/2003 | Burnside et al. | 606/41 |
| 6,730,078 | B2 * | 5/2004 | Simpson et al. | 606/34 |
| 6,855,141 | B2 * | 2/2005 | Lovewell | 606/34 |
| 7,029,470 | B2 * | 4/2006 | Francischelli et al. | 606/34 |
| 7,115,123 | B2 * | 10/2006 | Knowlton et al. | 606/41 |
| 7,217,269 | B2 * | 5/2007 | El-Galley et al. | 606/34 |
| 7,226,447 | B2 * | 6/2007 | Uchida et al. | 606/34 |
| 7,261,709 | B2 * | 8/2007 | Swoyer et al. | 606/41 |
| 7,282,048 | B2 * | 10/2007 | Goble et al. | 606/34 |
| 7,300,436 | B2 * | 11/2007 | Penny et al. | 606/34 |
| 7,303,557 | B2 * | 12/2007 | Wham et al. | 606/34 |
| 7,344,532 | B2 * | 3/2008 | Goble et al. | 606/34 |
| RE40,388 | E * | 6/2008 | Gines | 606/34 |
| 2003/0199863 | A1 * | 10/2003 | Swanson et al. | 606/40 |
| 2004/0138654 | A1 * | 7/2004 | Goble | 606/34 |
| 2004/0260279 | A1 * | 12/2004 | Goble et al. | 606/34 |
| 2005/0177150 | A1 * | 8/2005 | Amoah et al. | 606/34 |
| 2006/0111699 | A1 * | 5/2006 | Neuberger | 606/10 |
| 2006/0217700 | A1 * | 9/2006 | Garito et al. | 606/34 |
| 2006/0293649 | A1 * | 12/2006 | Lorang et al. | 606/32 |
| 2007/0060921 | A1 * | 3/2007 | Janssen et al. | 606/41 |

FOREIGN PATENT DOCUMENTS

| | | |
|---|---|---|
| DE | 3515622 A1 * | 11/1986 |
| EP | 256155 A1 * | 2/1988 |
| EP | 336742 A2 * | 10/1989 |
| WO | WO 9424949 A1 * | 11/1994 |

* cited by examiner

ELECTROSURGICAL SYSTEM

FIELD OF THE INVENTION

The present invention relates to an electrosurgical system and, more specifically, to an electrosurgical system capable of dynamically modulating the duty ratio of a power signal driving a probe of the system so as to maintain an operating condition effective for tissue ablation while preventing the power signal driving the probe from having an average power level that exceeds a predetermined limit.

BACKGROUND OF THE INVENTION

Electrosurgical systems have been used for a number of years in surgical procedures to cut and shape tissue at the surgical site while minimizing blood loss. As illustrated in the example of FIG. 1, a typical electrosurgical system includes an electrosurgical probe 12 (hereafter referred to simply as "probe") and a control console 14. The probe 12 generally comprises an elongated shaft 16 with a handle 18 at one end and a tip 20 at the opposite end. A single active electrode 19 is provided at the tip 20 if the probe 12 is of a "monopolar" design. Conversely, the probe 12 may be provided with both an active electrode 19 and return electrode 21 at the tip 20 if the probe is "bipolar" in design. The probe 12 connects to controller 14 by means of a detachable cable 22. The current for energizing the probe 12 comes from control console 14. When actuated, the control console 14 generates a power signal suitable for applying across the electrode(s) located at the tip 20 of the probe 12. Specifically, current generated by the control console 14 travels through the detachable cable 22 and down the shaft 16 to tip 20, where the current subsequently energizes the active electrode 19. If the probe 12 is monopolar, the current will depart from tip 20 and travel through the patient's body to a remote return electrode attached thereto. If the probe 12 is bipolar, the current will primarily pass from the active electrode 19 located at tip 20 to the return electrode 21, also located at tip 20, and subsequently back up the shaft 16 and through the detachable cable 22 to the control console 14.

Configuration of the control console 14 is carried out by means of an interface 15, while actuation and control of the probe 12 by the surgeon is accomplished by one or more switches 23 on the probe 12. One or more remote controllers, such as, for example, a footswitch 24 having additional switches 26 and 28, respectively, may also be utilized to provide the surgeon with greater control over the system 10. In response to the surgeon's manipulation of the various switches on the probe 12 and/or remote controller 24, the control console 14 generates and applies either a low power signal or high power signal to probe 12. As will be discussed in greater detail below, application of a low power signal to probe 12 results in the coagulation of the tissue adjacent the tip 20. In contrast, application of a high energy signal to probe 12 results in tissue ablation.

Although they have arguably revolutionized modern surgical practice, traditional electrosurgical systems continue to exhibit various deficiencies that make them difficult to use. For instance, there are frequently other types of instruments being utilized at or near the surgical site area of the patient's body making up the surgical site. These additional instruments, which can range from simple manipulators to sophisticated endoscopes, are often constructed from or contain electrically conductive material. As such, extra care must be taken when utilizing an electrosurgical probe at the surgical site so as to avoid having the probe coming in close proximity to, or in contact with another instrument, which can result in an arc of energy or increase in current that travels to the other instrument and transfers electrical current thereto.

In addition to the above deficiencies, electrosurgical systems can also be difficult to control. For instance, regulations frequently imposed on electrosurgical systems mandate that they not operate at power levels that exceed a predefined limit. However, maintaining an electrosurgical system in an ablative operating state can potentially result in the system operating at power levels that exceed the mandated maximum level. To assure that they operate at acceptable power levels, traditional electrosurgical systems are usually configured to monitor power levels, and in response to the detection of an excessive power level, modify the amount of voltage and/or current that they generate and use to drive their probe. However, such modifications to the voltage and/or current levels can result in operating instabilities that decrease the effectiveness of the probe.

To detect abnormal operating conditions that could potentially cause undesirable increases in power levels, traditional electrosurgical systems monitor certain operating parameters and calculate the electrical impedance or load that is encountered by the system and which represents the conditions existing at the tip of the probe. However, due to inherent delays in the process, the determination of impedance is found to not always be the most effective means of detecting undesirable conditions.

SUMMARY OF THE INVENTION

The present invention relates to an electrosurgical system comprising, among other things, a control console to which detachably connects one or more electrosurgical probes capable of coagulating and ablating tissue.

In one embodiment, the control console generates a selectively variable power signal having a duty cycle that is dynamically modulated so as to maintain an average power level that is lower than a predefined maximum power level.

According to another embodiment, an electrosurgical system for coagulating and ablating tissue incorporates both an impedance monitoring system and a current monitoring system as means to detect potentially undesirable situations where the probe of the system may be unintentionally discharged.

A third embodiment discloses an electrosurgical system incorporating impedance monitoring that operates in a "sputter" mode. Upon first activation of the electrosurgical system, the impedance monitor measures the impedance of a target area utilizing a relatively low power level. Only after detecting a "safe" impedance does the system increase the power for normal operation.

Disclosed in a fourth embodiment is an electrosurgical system that incorporates a non-volatile memory into the probe. Stored within the memory is probe-specific operating parameter data that aids in the automatic configuration of a controller. Data concerning the usage and restrictions of the probe can also be stored. In addition, data representing controller software updates can also be contained within the memory. Upon connection of the probe to the controller, the controller retrieves the software and proceeds to update.

BRIEF DESCRIPTION OF THE DRAWINGS

One or more embodiments of the present invention are illustrated by way of example and not limitation in the figures of the accompanying drawings, in which like references indicate similar elements and in which.

DETAILED DESCRIPTION

Figure 1:
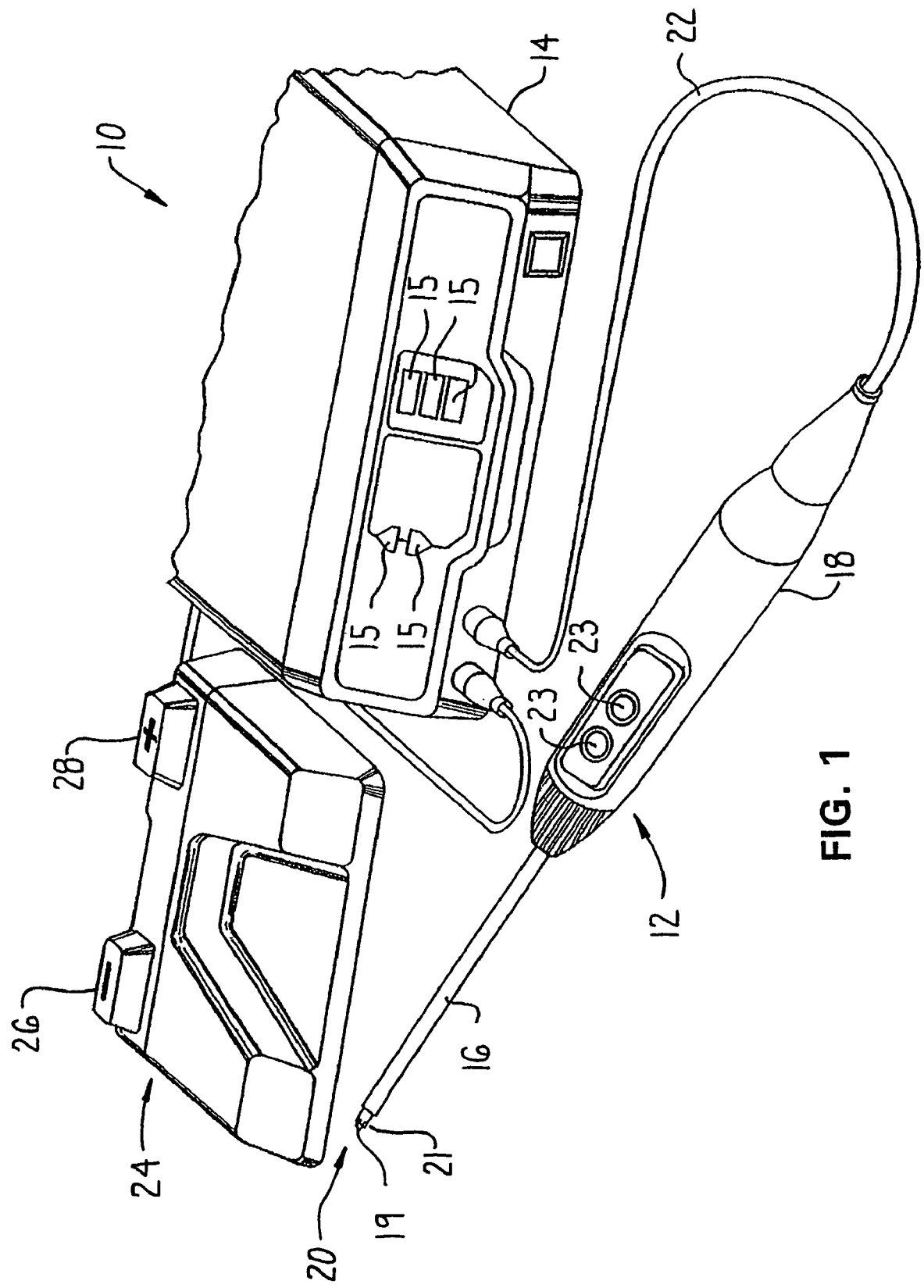
FIG. 1 depicts a typical electrosurgical system that includes a control console that detachably connects to an electrosurgical probe as well as remote footswitch control.

As previously discussed, electrosurgical systems function by providing electrical energy to one or more attached electrosurgical probes. More specifically, an electrosurgical generator, typically incorporated into the control console of the system, provides power to the attached probe in the form of a high frequency alternating current. This electrical current travels down to the active electrode located at the tip of the probe, where at least a portion of the electrical energy is transformed to thermal energy.

Underlying Electrical Principles

Operation of an electrosurgical system such as the one disclosed in the present invention can be analyzed in view of two relationships.

The first relationship is described by Ohm's law, which in simplest terms, is represented by the equation $(V=I \times R)$ [or alternatively $(V=I \times Z)$], where:

I=electrical current;
R=resistance or impediment to the current [hereafter referred to as Impedance (Z)]; and
V=voltage or force required to "push" the current through the impedance.

The second relationship is actually the definition of power (P), which can be calculated by the equation $(P=I \times V)$. The resultant product of current (I) and voltage (V) represents the amount of energy that is transferred within a defined period of time.

Coagulation vs. Ablation

Electrosurgical systems are able to affect tissue by means of either ablation or coagulation. Tissue ablation allows the electrosurgical cutting of tissue, and is achieved when a high power electrical signal having a sufficiently large voltage (e.g., 200V) is generated by the control console and directed to the attached probe. Application of the high power signal to the probe results in a large voltage difference between the two electrodes located at the tip of the probe (presuming a bipolar probe), with the active electrode being generally 200V more than the passive or return electrode. This large voltage difference leads to the formation of an ionized region between the two electrodes, establishing a high energy field at the tip of the probe. Applying the tip of the probe to organic tissue leads to a rapid rise in the internal temperature of the cells making up the neighboring tissue. This rapid rise in temperature near instantaneously causes the intracellular water to boil and the cells to burst and vaporize, a process otherwise known as tissue ablation. An electrosurgical "cut" is thus made by the path of disrupted cells that are ablated by the extremely hot, high energy ionized region maintained at the tip of the probe.

An added benefit of electrosurgical cuts is that they cause relatively little bleeding, which is the result of dissipation of heat to the tissue at the margins of the cut and produces a zone of coagulation along the cut edge.

In contrast to tissue ablation, the application of a low power electrical signal having a relatively low voltage to the active electrode located at the tip of the probe results in coagulation. Specifically, the lower voltage difference established between the active and return electrodes results in a relatively slow heating of the cells, which in turn causes desiccation or dehydration of the tissue without causing the cells to burst.

Operating Limitations

Frequently, regulations directed to the surgical field impose a target power level or maximum limit at which an electrosurgical system can operate. In response to these regulations, manufacturers configure their electrosurgical systems to operate at various power levels up to but not exceeding a selected maximum limit. For example, guidelines may require that an electrosurgical system operate at an average power level of no more than 400 W over any one second interval of time.

In reality, many factors must be considered before a determination can be made as to what an average maximum power level should be for an electrosurgical system. However, for illustrative purposes, the remainder of the disclosure will presume that a 400 W maximum average power limit has been imposed upon the present invention. As such, Applicants' electrosurgical system should operate in such a manner that the control console variably drives the attached probe so that an average power of the probe over a defined interval of time does not exceed 400 W.

Power Regulation in Coagulation Mode

According to a first embodiment, the present invention can be directed by a surgeon to operate in a coagulation mode. When in this operating state, the electrosurgical probe can, for example, be used to stop the bleeding of small blood vessels by applying the tip of the probe to the bleeding region and thereby coagulating the blood.

While operating in coagulation mode, the control console of the system is configured to drive the attached probe at a low, but constant, power level. Due to inherent varying conditions in tissue (i.e., the presence of connective tissue verses fatty tissue, as well as the presence or absence of saline solution), the impedance or load that the system experiences may vary. According to Ohm's law, a change in impedance will result in a change in current levels and/or a change in voltage levels, which in turn, will result in changing power levels. If the operating power level of the system changes by more than a predefined amount, the control console will attempt to compensate and return the power back to its originally designated level by regulating either the voltage and/or current of the power signal being generated by the console and used to drive the attached probe.

Power Regulation in Ablation Mode and Modulation of Duty Cycle

According to a second embodiment, the present invention can be directed by a surgeon to operate in a tissue ablation mode. When in this operating state, the electrosurgical probe is driven at relatively high power levels and can be used to "cut" tissue.

While operating in tissue ablation mode, the control console of the system is configured to drive the attached probe at as high a power level as possible without exceeding a maximum average power level, which in continuing on with the previous example, is presumed to be 400 W.

However, unlike coagulation mode, operation of the electrosurgical system in ablation mode is subject to a greater chance that the probe be driven to power levels that exceed an elected maximum limit. This is a result of the probe already being driven to high power levels, thereby leaving very little "buffer" to accommodate fluctuations. Thus, both expected variations, such as varying tissue impedance levels, as well as unexpected variations, such as the undesirable arcing of the active electrode due to the tip of the probe being brought in proximity to another surgical instrument, can result in the system operating at an average power level that exceeds an elected maximum limit.

In addition, fluctuations in voltage and current levels due to the inherent nature of electrosurgical applications can increase the risk of the electrosurgical probe being driven to an average power that exceeds a maximum limit. Specifically, there is a need to drive an electrosurgical probe with both high current levels as well as high voltage levels in order to initiate and maintain an ionized, high energy field at the tip of the probe. In order to initiate the high energy field, it is necessary for the control console to drive the attached electrosurgical probe at a maximum voltage so as to establish the required voltage difference between the active and return electrodes, thereby promoting creation of the ionized, high energy field. However, the subsequent formation of the high energy field leads to a drop in the impedance of the system, and thus an increase in current. Consequently, an electrosurgical system operating in a high energy ablation mode has to initially be driven at a maximum voltage to initiate formation of an ionized high energy field, but then effectively switched to a maximum current requirement once a stabile field is formed.

To try and prevent an average operational power level from exceeding an established limit, the traditional electrosurgical systems attempt to stabilize or return an elevated power level back to normal through regulation of either the current levels and/or voltage levels of the power supply signal. However, as previously discussed, the formation and maintenance of a stable high energy field at the tip of the probe requires sufficiently high voltage and current levels that do not fluctuate significantly. As a result, the modulation of current levels and/or voltage levels in previous systems allowed for these systems to operate with an average power level that does not exceed an established maximum limit. However, the same modulation of current and voltage levels also resulted in the ionized high energy field maintained at the tip of the probe becoming unstable and unreliable when the systems are operated in ablation mode.

In contrast to traditional systems, the present invention does not attempt to regulate high power levels exclusively through modulation of the voltage and current levels making up the power supply signal. Instead of only manipulating a component of the power signal, the present invention can modulate the entire signal as a whole, turning the signal on and off in a manner similar to a pulse width modulated (PWM) signal. Furthermore, the power signal is dynamically modulated on and off so as to behave like a PWM signal having a variable duty cycle. As a result, the percentage of time that the power signal is "on", compared to the percentage of time that the signal is "off", will vary depending on the percentage of time that the power levels of the signal exceed the maximum limit over a predetermined interval of time.

Consequently, the duty cycle of the power signal is dynamically modulated so that even though the power levels of the signal may briefly exceed the maximum power limit for a portion of time during a specified interval, the average power level over that interval of time remains acceptable. For example, according to one particular embodiment, an electrosurgical system may operate in 50 millisecond periods, with the duty cycle of the power signal potentially varying from one period to the next. If during a one second period, the power level of the signal driving the probe exceeded a maximum power limit, then the duty cycle would be adjusted so that the signal was turned off for at least a portion of the next period in order to compensate for the larger power level that occurred during the first period. As a result of the dynamic duty cycle, the average power level of the signal never exceeds the maximum safe limit.

Figure 2:
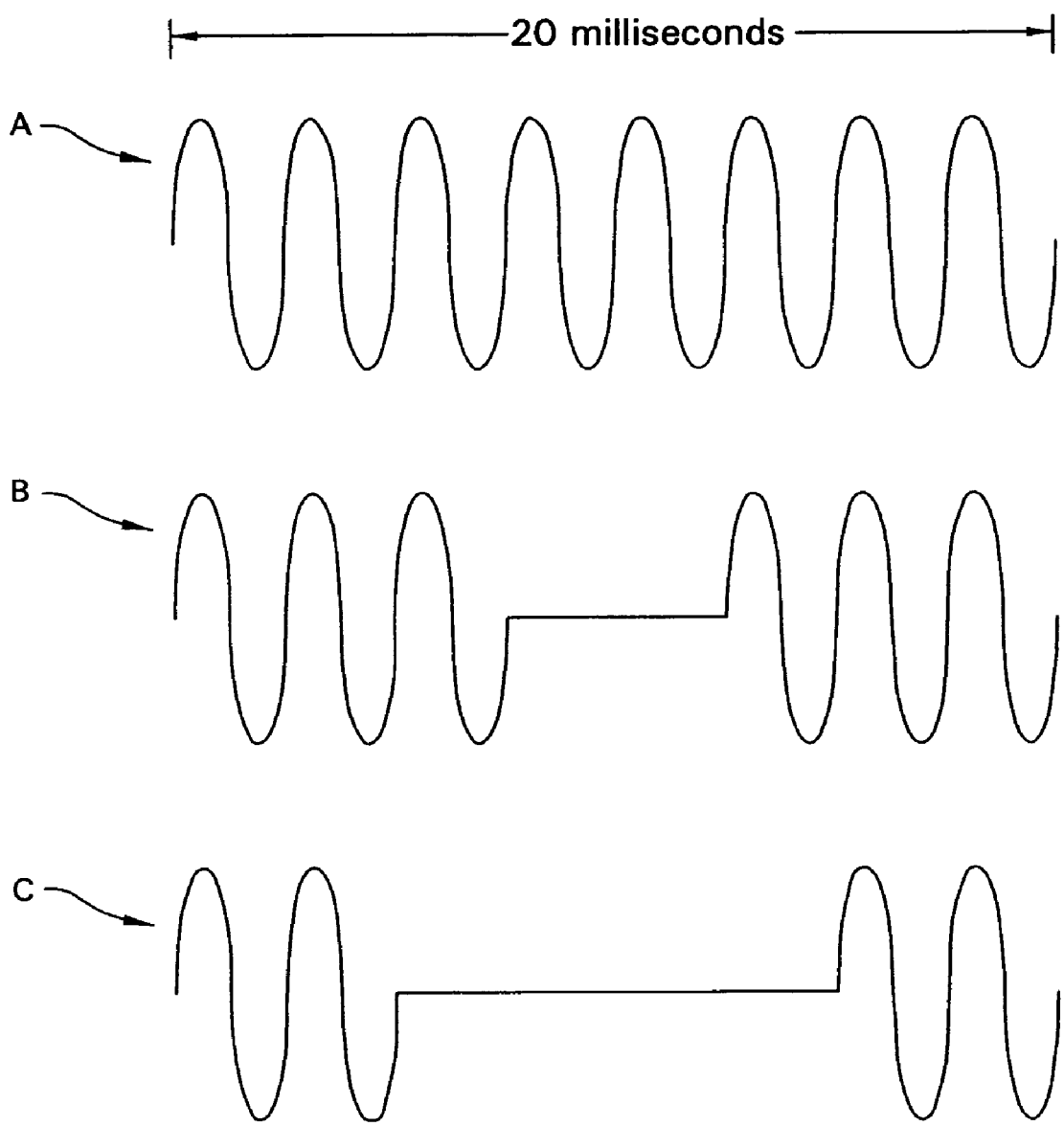
FIG. 2 depicts several examples of a high frequency power signal generated by the control console over a 20 millisecond period of time and used to drive the attached probe.

To further illustrate the above point, see FIG. 2, which depicts several examples of a high frequency power signal generated by the control console over a 20 millisecond period of time and used to drive the attached probe. Signal A is a power signal in the form of a 200 KHz sine wave. No modulation of signal A is present with respect to a signal duty cycle, resulting in a power signal that is continuously on (i.e., 100% duty cycle) for the entire 20 millisecond duration.

Signal B is similar to signal A, but has been briefly modulated roughly half-way through the 20 millisecond period. In this instance, for example, changing environmental variables may have resulted in the power level of the signal briefly exceeding an established maximum limit during the previous 20 millisecond period (not shown). To compensate for this prior spike in power level and assure that the average power of the signal does not exceed a maximum limit, the system briefly modulates signal B during the next 20 millisecond period (shown), effectively turning the signal off for a moment. Thus, for example, signal B is modulated or turned off for approximately 5 milliseconds during the 20 millisecond period depicted, resulting in the signal effectively having a 75% duty cycle for the period shown.

To compensate for power level spikes that are larger in magnitude or longer in duration, the system dynamically modulates the duty cycle of the power signal during the next monitoring interval to effectively turn off the signal for a longer period of time. For example, signal C of FIG. 2 is similar to signal B, but is modulated to have a lower duty cycle, resulting in signal C being turned off for a longer period of time during the 20 millisecond interval shown.

By dynamically adjusting a duty cycle of the power signal, the average power of the signal can be maintained below an established maximum power limit. Furthermore, it has been observed that the ionized high energy field maintained at the tip of the probe does not collapse, but remains stable, if the effective duty cycle of the power signal is modulated quickly enough (i.e., turning the signal on or off in increments of 50 milliseconds over a 1 second period).

Increased Safety Though Monitoring of Impedance and Current Spikes

In a typical, modern day surgery, the surgical site or area of the patient's body being operated upon is usually quite small. In contrast, the number of surgical instruments utilized during a normal surgery continues to grow. For example, during a routine abdominal surgery, the surgical site may be worked upon by numerous instruments ranging from endoscopes and manipulators to clamps, probes and suction, to name just a few. In such an environment, extra precaution must be taken whenever an electrosurgical probe is being used to cut or cauterize tissue at the surgical site. With contact between the electrosurgical probe and another surgical instrument, or even having the probe being brought within a relative close proximity to another surgical instrument, can lead to an undesirable transfer of energy from the electrosurgical probe to the other instrument.

To minimize the electrical currents discussed above, the present invention according to another embodiment can incorporate one or more different types of monitoring systems for detecting sudden changes in different electrical properties that may indicate an undesirable situation.

Figure 3:
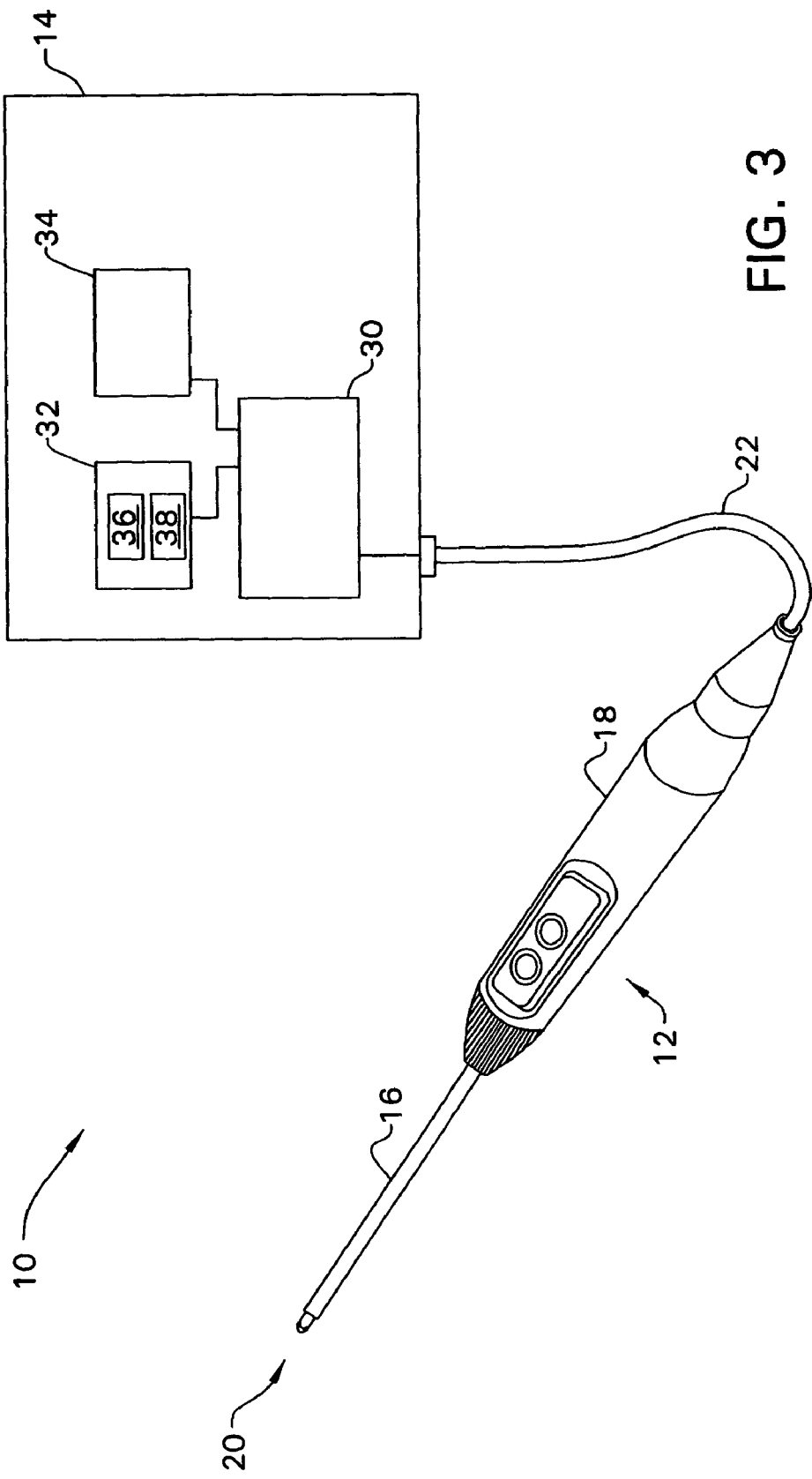
FIG. 3 depicts an electrosurgical system incorporating both an impedance monitoring system and an electrical current monitoring system.

As illustrated in FIG. 3, a first monitoring system 32 can comprise a circuit for measuring the impedance being encountered by the electrosurgical probe. Generally speaking, the greater the electrical conductivity of an object, the lower its impedance. As the electrosurgical probe of the present embodiment is brought closer to metal, such as another surgical instrument, the measured impedance steadily decreases. To prevent an undesirable discharge, the electrosurgical system is configured to automatically shut-off the generator 30 driving probe 12 when the measured impedance drops below a predetermined threshold.

According to one example, the impedance monitoring circuit 32 comprises a system 36 for generating a signal representative of voltage, as well as a signal representative of the inverse of current. Each of these signals is subsequently provided to a multiplier 38, which generates a product of the two signals that represents a measured resistance or impedance. Alternatively, virtually any other device or circuit capable of measuring impedance could be incorporated into the current embodiment.

A second monitoring system 34 can comprise virtually any device or circuit capable of monitoring an electrical current. The advantage of the second monitoring system is that current rises rapidly, allowing for easier detection. A current monitoring system is also advantageous as it involves a single direct measurement that can be rapidly carried out. In contrast, impedance measuring is much less responsive as it requires not only the measuring of two electric signals, but also accurate ratio calculations.

According to a further embodiment, both impedance monitoring and current monitoring are incorporated into the disclosed electrosurgical system 10. However, depending on the operating state of the system, one such monitoring system may be found to be more useful than the other. For instance, the current monitoring system is found to provide much quicker detection results when the electrosurgical system is operating in a tissue ablation mode where relatively large currents are generated. In contrast, impedance monitoring is more effective when the electrosurgical system is operating in a coagulation mode. Current monitoring is less desirable in this situation due to the relatively low power levels generated by the system when operating in coagulation mode. As a result of these relatively low power levels, the system never generates a high enough level of current that can be accurately detected by the current monitoring system. Accordingly, impedance monitoring is relied upon when the system is operating in a coagulation mode.

Utilizing a Sputter Mode Detection System to Increase Safety During Initial Activation of the Probe More traditional electrosurgical systems usually do not initiate any form of safety precautions, such as current monitoring or impedance monitoring, until after the probe has been activated and utilized once so as to establish a first measurement. As a result, these prior art systems provide little or no protection during the first use of the system.

Figure 4:
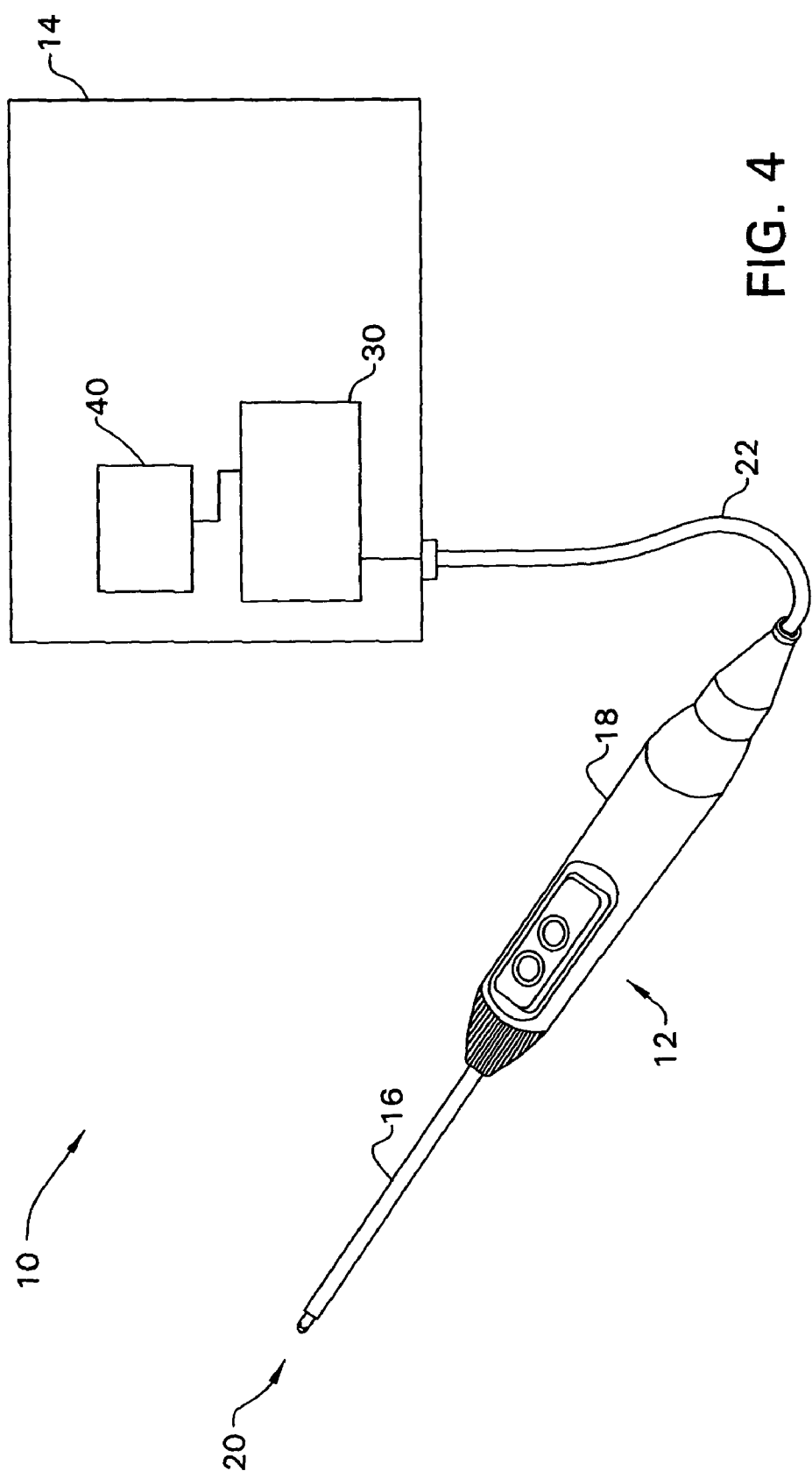
FIG. 4 depicts an electrosurgical system incorporating an impedance monitoring system capable of determining the impedance of an area upon first activation of the probe at a relatively low power level.

In contrast to more traditional systems, the current embodiment of the present invention, as illustrated in FIG. 4, incorporates an impedance monitoring system 40 that operates in a "sputter" mode and which protects a user during initial activation of the system. Specifically, upon a user first activating the system and applying the attached probe to a target area, the system first measures the impedance of the target area by causing the generator 30 to activate the attached probe 12 at a relatively low power level. If a "safe" impedance level is detected (i.e., indicating that the probe is in contact with tissue), then the impedance monitoring system 40 causes the generator 30 to increase the power to the probe, driving it at substantially higher power levels needed for normal operation. The low power impedance monitoring and transition to normal operating power levels occur substantially in real time so as not to be noticeable by the user.

Incorporation of Non-Volatile Memory and Automatic Configuration of Different Attachable Probes In a further embodiment of the present invention, a non-volatile memory device 50 (such as a NOVRAM, ROM or Flash memory, to name just a few) is incorporated into each probe that can be attached to and driven by a control console of the system. Also incorporated into each probe is a data reader/writer 51 capable of retrieving information from the memory device as well as writing information to the memory device. According to an additional embodiment, the reader/writer may incorporate RFID or other wireless-based technology.

Figure 5:
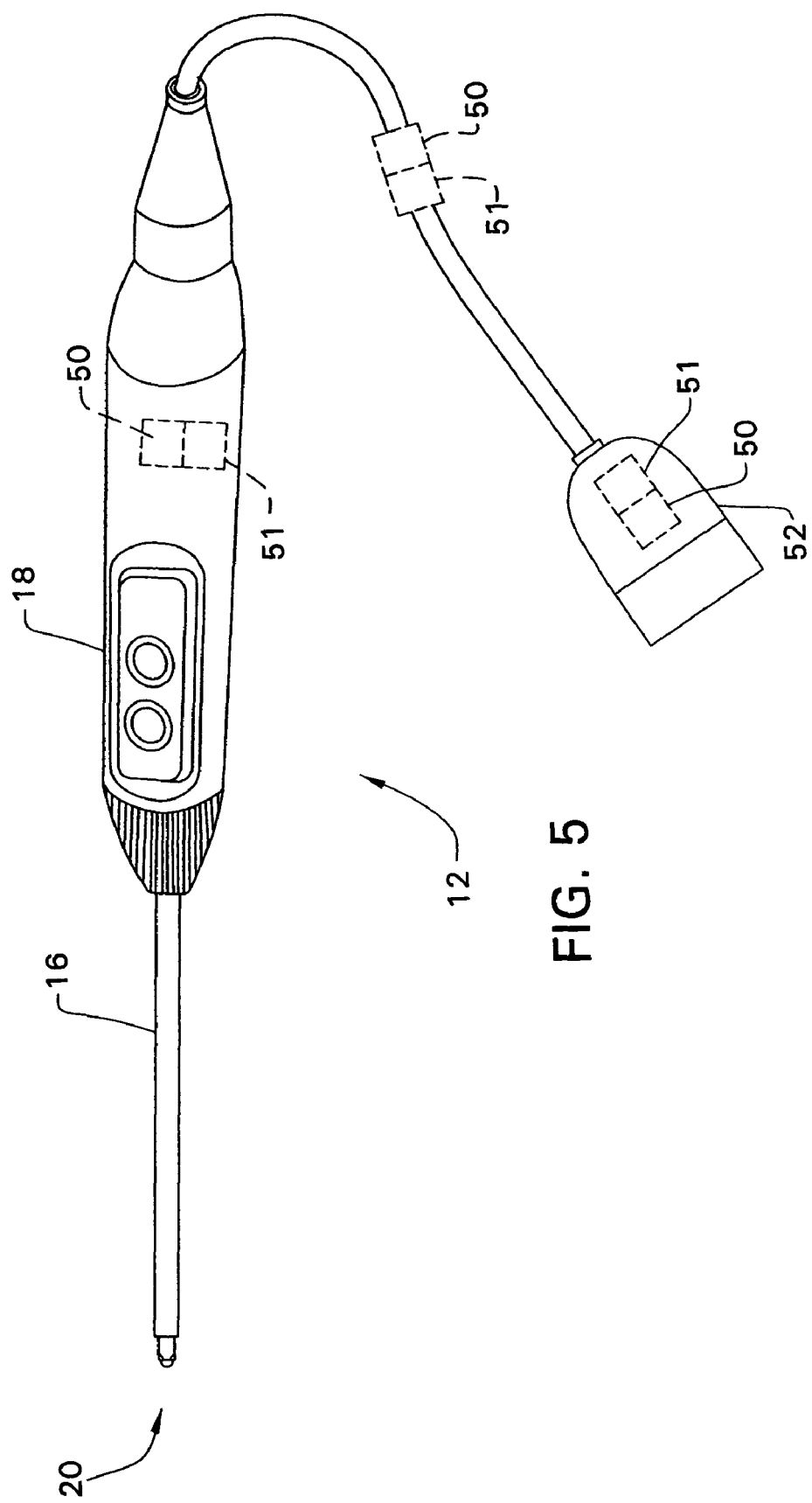
FIG. 5 depicts an electrosurgical probe incorporating a non-volatile memory and reader/writer for interfacing with the memory.

As illustrated in FIG. 5, a non-volatile memory device 50 and reader/writer 51 can be incorporated into the body 18 of the probe 12, or alternatively, incorporated into or on the cable 22 that is part of the attachable probe and which is used to connect the probe to the control console of the system. Alternatively, the memory device 50 may be configured so as to be incorporated into or on the communication port 52 that is located at the free end of the attachable probe's cable and which is used to interface the cable with a corresponding port on the controller.

During manufacturing of the attachable probe, data representing probe-specific operating parameters is loaded into the memory device. Upon connection of the attachable probe to the control console of the system, the data stored in the probe's non-volatile memory can be accessed by the reader and forwarded on to the controller. As such, once a probe is connected, the controller can access the configuration data of the probe specifically attached and can automatically configure itself based on the operating parameters of the probe.

Beyond probe-specific operating parameters, the memory device within each attachable probe can store additional data concerning usage of the probe. This usage data can comprise a variety of information. For example, usage data may represent the number of times a probe has been used, or the duration of time that the probe has been activated overall or at different power levels. Additional usage data may restrict the amount of time that a specific attachable probe can be used. For instance, a specific probe may be restricted to a total of 1 hour of accumulated use. Alternatively, a probe may be programmed so it can only be used for a limited duration of time starting from the moment the probe was first attached to a control console and powered up. For example, a probe may be programmed so that it only functions for a 24 hour period starting from when the probe is first activated. Based on a clock maintained within the control console, a time stamp is written to the memory device of the probe when the probe is attached to the console for the first time and powered up. Any later attempted use of that probe will trigger a comparison of the stored time stamp to the current time reported by the control console, and if the allotted amount of time has already passed, the system will not allow the probe to be used.

Alternatively, a specific probe may be dynamically restricted, so that the overall amount of time allocated for use of the probe will vary depending not only on the amount of time the probe has been used, but also the power levels that the probe was driven at during its use. As such, a specific attachable probe may be limited to 1 hour of use if always driven at a maximum power, but may be usable for 3 hours if all prior uses occurred at substantially lower power levels.

In addition to usage data, the memory device can store information concerning any errors that were encountered during use of the probe. For example, the failure of a probe to activate would lead the control console to issue and store one or more error codes into the probe memory. Technicians can later retrieve these error codes to aid in their examination of the failure.

In addition to probe-specific operating parameters and usage data, the memory device incorporated into each probe may also be programmed by the manufacturer to include software scripts or updates for the control console of the system. Thus, for example, a user obtains a new probe and proceeds to attach it to their control console that is a year or two old. Upon attachment of the new probe, the controller queries the memory device within the new probe for probe-specific operating parameters. In addition, the controller recognizes and proceeds to retrieve from the probe's memory certain data or scripts. Upon retrieval, the scripts are automatically run on the controller, resulting in one or more sections of the controller's operating system and/or associated databases to be updated with new information. In this manner, manufacturers will be able to push updates out to products such as an electrosurgical system by storing the update within the memory of an attachable probe or accessory that plugs into the controller.

While the invention has been specifically described in connection with certain specific embodiments thereof, it is to be understood that this is by way of illustration and not of limitation, and the scope of the appended claims should be construed as broadly as the prior art will permit.

What is claimed is:

1. A method of energizing an electrosurgical probe so as to allow for the manipulation of tissue, comprising the steps of:
    establishing a maximum acceptable average power level that the electrosurgical probe should not exceed;
    energizing the electrosurgical probe with a power signal for a first defined period of a first interval;
    interrupting the power signal for a second defined period of the first interval when an actual power level of the power signal during the first defined period of the first interval exceeds the established maximum acceptable average power level for the first interval; and
    when the actual average power level over the first interval exceeds the maximum acceptable average power level, outputting the power signal during a second interval subsequent to the first interval such that the actual average power level of the power signal over the first interval combined with the actual average power level over the second subsequent interval does not exceed the maximum acceptable average power level.

2. The method according to claim 1, wherein each said interval has a duty cycle consisting of the first defined period and the second defined period, wherein the second defined period of the second subsequent interval is different than the second defined period of the first interval, the method further comprising the step of modulating at least one of voltage levels and current levels making up the power signal, in combination with dynamically modulating the duty cycle of the power signal, to regulate the average power level of the probe.

3. The method according to claim 1, wherein the second interval includes a first defined period with the power signal applied and a second defined period when the power signal is interrupted, and wherein the first defined period and the second defined period of each said interval together define a duty cycle of the interval that is capable of being varied automatically for different said intervals, and wherein each said interval has the same length of time.

4. A method of energizing and monitoring impedance in an electrosurgical system configured to ablate or coagulate tissue within a target area by an electrosurgical probe, comprising the steps of:
    establishing a maximum acceptable average power level that the electrosurgical probe should not exceed;
    energizing the electrosurgical probe to a relatively low power level in response to a user first activating and applying the probe to the target area;
    determining an impedance of the target area;
    de-energizing the electrosurgical probe if the determined impedance is less than a predefined value;
    energizing the electrosurgical probe to output a power signal at a higher power level greater than the maximum acceptable average power level necessary for tissue ablation, if the determined impedance is greater than a predefined value;
    subsequently energizing the electrosurgical probe to ablate tissue with a power signal having a value greater than the maximum acceptable average power level for a first defined period of a first interval;
    interrupting the power signal for a second defined period of the first interval when an actual measured power level of the power signal for the first defined period of the first interval exceeds the established maximum acceptable average power level for the first interval; and
    when the actual average power level over the first interval exceeds the maximum acceptable average power level, outputting the power signal during a second interval subsequent to the first interval, such that the actual average power level of the power signal over the second interval is less than the established maximum acceptable average power level for the electrosurgical probe so that the actual average power level of the first interval combined with the actual average power level over the second subsequent interval does not exceed the maximum acceptable average power level.

5. The method according to claim 4, wherein the steps of energizing the probe to a low power level, determining impedance, and energizing the probe to a high power level occur substantially in real time so as not to be noticeable by a user.

6. The method according to claim 4, wherein the second interval includes a first defined period when a power signal is applied and a second defined period when the power signal is interrupted, wherein the first and second defined periods of each said interval define a duty cycle, and wherein each said interval has the same length of time.

7. A method of energizing an electrosurgical probe comprising:
    providing a coagulation power level for use in driving the electrosurgical probe to coagulate tissue during a coagulation mode;
    providing a maximum acceptable average power level that an average power level of the electrosurgical probe should not exceed for ablating tissue during a tissue ablation mode;
    selecting the tissue ablation mode;
    outputting a power signal having a power level greater than the maximum acceptable average power level to the electrosurgical probe to ablate tissue during a first time period of a first time interval, applying no power signal to the electrosurgical probe during a second time period of the first interval, wherein for the first interval an actual average power level for the power signal exceeds the maximum acceptable average power level;

automatically controlling the actual average power level during a first time period of a second time interval to be greater than the maximum acceptable average power level; and applying no power signal to the electrosurgical probe during a second time period of the second interval so that the actual average power level for the second interval is less than the maximum acceptable average power level, wherein the actual average power level over the first and second time intervals combined is not greater than the maximum acceptable average power level.

8. The method according to claim 7, wherein said first and second time periods of each said interval together define a duty cycle.

9. The method according to claim 8, wherein the step of automatically controlling the actual average power level during the second time interval comprises changing the duty cycle to lessen the first time period of the second interval that provides the power signal to the electrosurgical probe.

10. An electrosurgical system for coagulating and ablating tissue, comprising:
a control console;
an electrosurgical probe that detachably connects to the control console;
a generator disposed in the control console for generating a variable power signal for energizing the electrosurgical probe;
a first monitoring system disposed in the control console and in communication with the generator, the first monitoring system being configured to determine an impedance of the tissue being acted upon by the electrosurgical probe and for terminating the energizing of the electrosurgical probe if the determined impedance falls below a predefined value during tissue coagulation; and
a second monitoring system acting independently from the first monitoring system and disposed in the control console and in communication with the generator, the second monitoring system being configured to detect changes in an amount of electrical current making up the power signal and for terminating the energizing of the electrosurgical probe if a detected increase in the amount of electrical current exceeds a predefined amount during tissue ablation.

11. The electrosurgical system according to claim 10, wherein energizing of the electrosurgical probe during tissue coagulation is not terminated on the basis of the second monitoring system, and energizing of the electrosurgical probe during tissue ablation is not terminated on the basis of the first monitoring system.

12. The electrosurgical system according to claim 10, further comprising:
a non-volatile memory device in the probe for storing at least one of probe-specific operating parameters and probe usage data; and
a data reader/writer for retrieving information from the memory device and writing information to the memory device.

13. The electrosurgical system according to claim 12, wherein the non-volatile memory device is incorporated into a body of the probe, the electrosurgical probe comprising a handle, an elongated shaft projecting from an end of the handle, and an electrode disposed at a tip end of the shaft.

14. The electrosurgical system according to claim 12, wherein the non-volatile memory device is incorporated into a cable of the probe, the electrosurgical probe comprising a handle, an elongated shaft projecting from an end of the handle, and an electrode disposed at a tip end of the shaft.

15. The electrosurgical system according to claim 12, wherein the non-volatile memory device is incorporated into a communication port located at a free end of a cable of the probe and used to interface the cable with a corresponding port on the control console.

16. The electrosurgical system according to claim 12, wherein the control console accesses the information upon connection of the probe and automatically configures itself based on the accessed information.

17. The electrosurgical system according to claim 16, wherein the control console will energize the probe so long as the probe usage data indicates accumulated use of the probe has not exceeded a predefined amount of time.

18. The electrosurgical system according to claim 17, wherein the predefined amount of time is dynamically adjusted based on the amount of time the probe has been used in combination with power levels the probe was driven at during its use.

19. The electrosurgical system according to claim 16, wherein the control console is capable of storing into the memory, via the data reader/writer, information concerning errors encountered during use of the probe.

20. The electrosurgical system according to claim 16, wherein the memory stores software updates for the control console that automatically run upon attachment of the probe to the control console.

* * * * *